United States Patent [19]
Kawarizadeh et al.

[11] Patent Number: 5,903,222
[45] Date of Patent: May 11, 1999

[54] WET GARMENT DETECTOR

[75] Inventors: Behrouz Kawarizadeh; Aram Kovach, both of Columbus; Rod K. Ghani, Granville, all of Ohio

[73] Assignee: Zaggie, Inc., Columbus, Ohio

[21] Appl. No.: 08/834,753

[22] Filed: Apr. 3, 1997

[51] Int. Cl.$^6$ ................................................ G08B 21/00
[52] U.S. Cl. ..................... 340/604; 340/573; 128/886; 604/361
[58] Field of Search ..................... 340/604, 573, 340/603, 605; 604/361, 364, 358; 200/61.04, 61.05; 128/885, 886; 361/271, 272, 280, 281, 502, 503, 515

[56] References Cited

U.S. PATENT DOCUMENTS

| | | | |
|---|---|---|---|
| 3,460,123 | 8/1969 | Bass | 340/604 |
| 4,106,001 | 8/1978 | Mahoney | 340/604 |
| 4,754,264 | 6/1988 | Okada et al. | 340/573 |
| 4,796,014 | 1/1989 | Chia | 340/573 |
| 4,800,370 | 1/1989 | Vetecnik | 340/573 |
| 5,137,033 | 8/1992 | Norton | 128/886 |
| 5,197,958 | 3/1993 | Howell | 604/361 |
| 5,264,830 | 11/1993 | Kline et al. | 340/604 |
| 5,266,928 | 11/1993 | Johnson | 340/604 |
| 5,469,145 | 11/1995 | Johnson | 340/604 |
| 5,469,146 | 11/1995 | Gurler | 340/605 |
| 5,557,263 | 9/1996 | Fisher et al. | 340/605 |

*Primary Examiner*—Jeffery A. Hofsass
*Assistant Examiner*—Toan N. Pham
*Attorney, Agent, or Firm*—James R. Eley, Esq.

[57] ABSTRACT

A garment diaper detector for detecting wetness conditions in diapers or undergarments comprising a capacitive sensor located within a housing and affixed to the exterior surface of the garment being monitored. The sensor is comprised of two substantially solid, coplanar conductor plates affixed to a common substrate and has a very high dynamic range. The inside of the garment becomes wet, the capacitance between the spaced conductors rises above a predetermined value whereupon the detector provides an output to a transmitter or an alarm. When the garment is being changed, the detector is removed from the exterior surface of the garment for reuse on the next. In one embodiment of the invention, multiple, uniquely addressed wetness detectors are employed to monitor the wetness conditions in a plurality of garments, such as in a hospital or nursing home. When a garment becomes wet, that unique address is transmitted to a central monitoring station which dispatches a care giver to change the garment. Additionally, the central monitoring station may be equipped with a modem which communicates the address of wet garments to pagers worn by care givers.

6 Claims, 5 Drawing Sheets

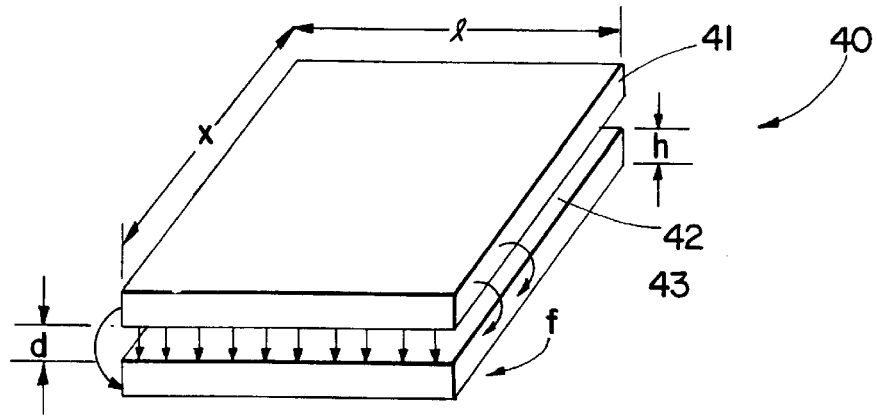
Fig. 5
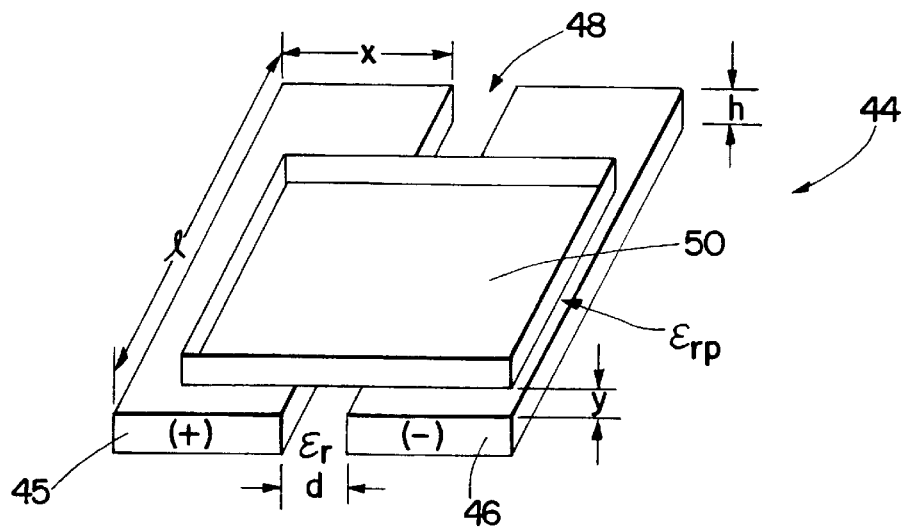
Fig. 6
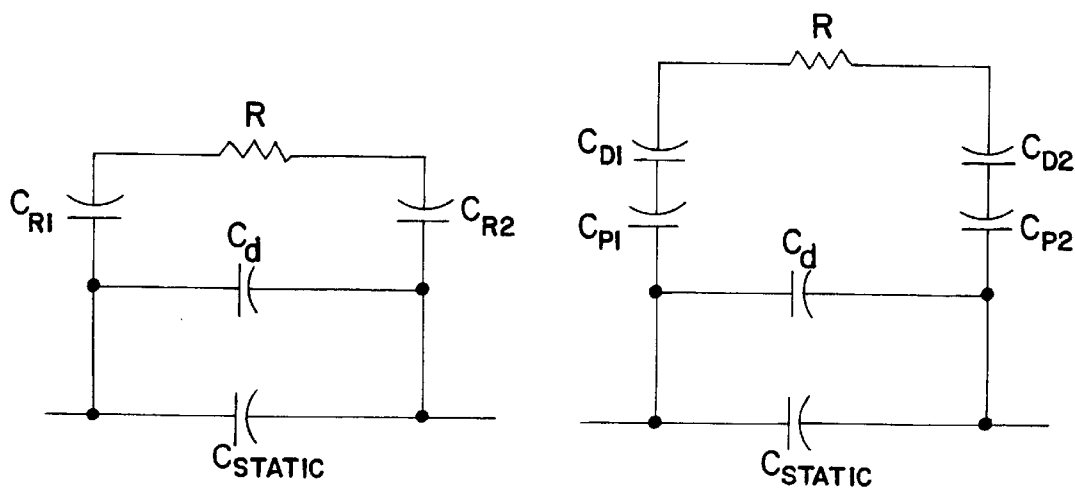
Fig. 7
Fig. 8

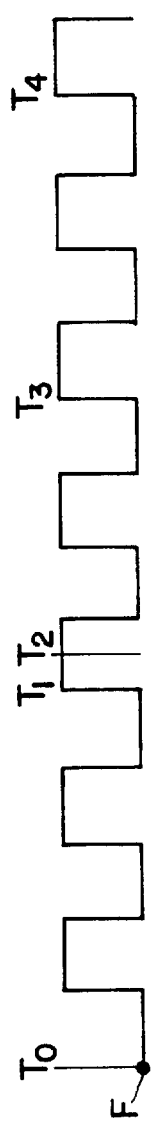
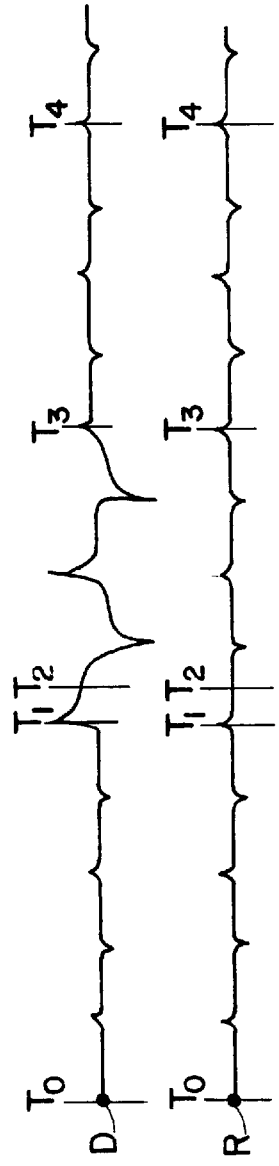
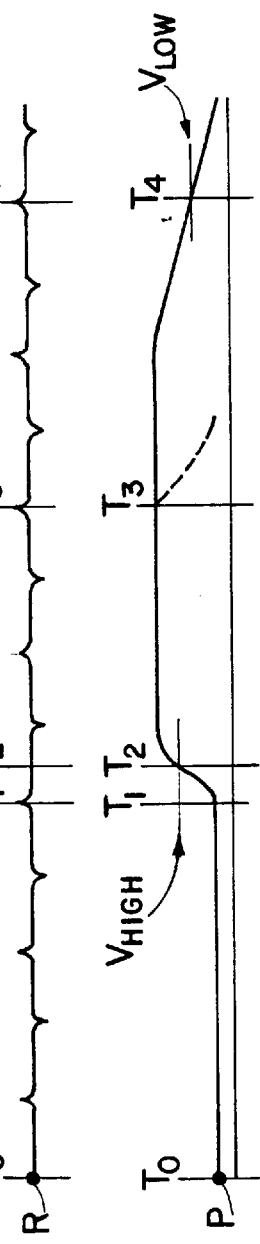
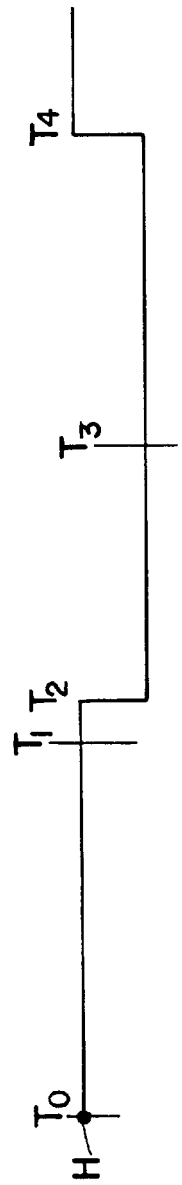
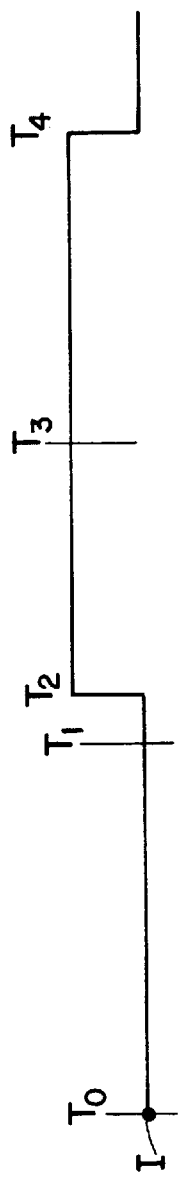
Fig. 10  Fig. 11  Fig. 12  Fig. 13  Fig. 14  Fig. 15

WET GARMENT DETECTOR

BACKGROUND OF THE INVENTION

1. Field of the Invention

This invention relates generally to a wetness sensing device for diapers and other undergarments to enable the prompt changing of the same when they become wet. In its particular aspects, the present invention relates to a reusable device containing a non-contacting capacitive sensor mounted on the external surface of any type of diaper and a transmitter for relaying the presence of a wetness condition to a remotely monitored station.

2. Description of the Prior Art

One of the primary causes of diaper rash is, of course, that diaper wearers frequently wet their diapers and, for one reason or another, remain in bodily contact with the wet diapers for prolonged periods before they are changed. While some diaper wearers may be able to communicate the presence of a wetness condition, a significant number of wearers, including infants and the aged, are not. Even then, by the time a communicative diaper wearer realizes the wetness, the effect of the wetness condition may have already caused or exacerbated a skin irritation.

The number of aged persons is increasing primarily due to improved health care. This has caused a corresponding increase in the number of bed-ridden patients, many of which wear disposable undergarments. For example, in care facilities, such as hospitals and nursing homes, it is estimated that approximately 30% of the patients are bed-ridden or otherwise incontinent and are thus required to wear diapers of some sort. For such patients, the timely changing of diapers is both an issue of comfort and hygiene.

It is desirable for a care provider to provide for both the comfort and hygiene of its patients. However, without the aid of electrical sensors, attendants in such a care facility must physically inspect for the presence of wetness in the diapers of their patients. This is often done according to a pre-determined schedule, regardless of the patient's urination schedule. Therefore, a patient who appears dry during a scheduled check may soon thereafter soil their diaper and be left to lie in the wet or soiled diaper until the next scheduled inspection. Also, checking on a predetermined schedule is both inefficient use of the attendants' time and leads to inconveniencing the patient more often than is necessary. Additionally, depending upon the amount of urination and how long since the discharge, the diaper may not appear to be wet to the attendant inspecting it, thus leaving the wearer in contact with a soiled garment.

Electrical alarm devices have previously been proposed as a means for informing an attendant that a wet diaper condition has occurred so that the diaper can be changed and the wearer's skin cleansed thus increasing comfort and reducing the likelihood of irritation. One example of such a proposed alarm device is disclosed in U.S. Pat. No. 3,460,123 issued to Bass. Bass shows a resistive-type of wet garment alarm system that employs a diaper formed with a pair of spaced conductive screens having an electrolyte disposed therebetween and a transmitter for producing a radio signal. The transmitter is electrically coupled to the screens and is adapted to produce a radio signal when the resistance between the screens falls below a predetermined level.

In use, the transmitter of Bass is secured to the upper waist portion of an infant's diaper, and the diaper is secured to its wearer with the pair of conductive screens positioned at the crotch portion of the diaper. When the diaper is wet by the wearer, urine flows into the crotch portion of the diaper and electrically bridges the space between the conductive screens thus reducing the resistance between the screens. This reduced resistance, in turn, actuates the transmitter to produce a radio signal for activating a remote alarm to alert a parent or attendant to the wet diaper condition.

Another system for detecting and signaling a wet diaper condition is disclosed in U.S. Pat. No. 4,106,001, issued to Mahoney, wherein a garment clip houses a resistive-type moisture detector and alarm. The garment clip is adapted to be clipped onto an exposed edge of a diaper or other garment to be monitored. An elongated strip of material is detachably connected at one end to the clip and is sized to be positioned in a region of the diaper subject to wetness such as, for example, the crotch region. The strip of material includes a pair of embedded spaced electrodes that are coupled to the detector/alarm. When urinated upon by the wearer of the undergarment, a partial electrical short circuit occurs between the electrodes at some point along the strip of material. This short circuit is detected by the moisture detector, which activates the alarm to provide an audible indication of urination by the infant or wearer.

Yet another wetness detector is disclosed in U.S. Pat. No. 4,754,264 issued to Okada et al. wherein a capacitive-type sensing unit is composed of a water permeable upper sheet, a water impermeable lower sheet, a pair of metal layers placed inside the diaper between the upper and lower sheets longitudinally through the crotch area, and an informing unit for powering the capacitor and processing the wetness detection signal. When the wearer urinates, wetness penetrates the permeable layer and affects the electrostatic capacitance of the capacitively-coupled metal layers in the diaper. The sensor is separated from the informing unit when the diaper is changed and is disposed of with the diaper.

A similar system is disclosed in U.S. Pat. No. 4,796,014 issued to Chia, wherein a safety pin with spaced electrical conductors is coupled to a resistive-type detector and alarm device attached to a diaper. When urine bridges the space between the electrical conductors of the safety pin, a detection circuit is completed, which, in turn, activates the alarm. The Chia device further includes a circuit to delay the sounding of the wetness alarm to ensure that it does not interfere with an infant's normal urination cycle.

Another wetness sensing device is disclosed in U.S. Pat. No. 5,469,145 issued to Johnson. Johnson shows a capacitive-type sensor with interleaved conductive plates of a sensing capacitor mounted on the outside of a housing which is then affixed to the external surface of the diaper being monitored. When the inside of the diaper becomes wet, the capacitance of the sensor changes and provides a signal to actuate a local alarm.

While these and similar devices have been somewhat successful in signaling a wet diaper condition, they still tend to exhibit numerous problems and shortcomings inherent in their respective designs. For instance, several of these devices include a pair of conductive electrodes built into the material forming the diaper itself. Such a configuration is shown in the patents of Bass and Okada et al. Obviously, manufacture of these types of diapers can be relatively expensive since special diaper forming machinery must be developed and implemented. Another common problem with prior art devices is that the detecting strips that reside in the diaper are configured as integral non-detachable elements of the detector and alarm circuits. With such a configuration, the entire device often must be discarded when the sensing strip becomes worn, which is inefficient and wasteful. Also, manufacturing the detection devices and alarms in some prior art devices can become complicated and costly. Finally, the mere fact that conductive electrodes must extend into the diaper to detect resistive or capacitive changes when the wearer wets is objectionable to many and, under the proper condition, may result in a mild shock to the wearer.

Of the capacitive types of detectors, the fact that the sensor may be located on the inside of the diaper is affected with the same problems as the intra-diaper resistive-type sensors. Requiring that the conductive plates of the capacitor to be disposed of with each diaper is also wasteful and expensive. Additionally, the device disclosed in Johnson teaches that the interleaved conductive plates of the sensing capacitor are mounted on the outside of a housing directly against the exterior surface of a diaper. Mounting of the sensor of the Johnson device directly against the surface of the diaper is necessary because of relatively high capacitance, i.e., low sensitivity, of the capacitive sensor design. This is undesirable since the plates may come into contact with the skin of the wearer thus triggering a false wetness condition. Additionally, the exposed capacitive plates are subject to becoming easily soiled since they are directly exposed.

Accordingly, there exists a continuing and heretofore unaddressed need for a sensitive wet diaper detector and alarm system that is usable with a conventional disposable or non-disposable diaper, is remotely monitorable, is inexpensive to produce, easy and convenient to use, does not necessarily require that conductive electrodes extend into the diaper itself, and that does not require expensive and bulky housings that must be secured to a wearer's garments. It is to the provision of such a wet diaper detector and monitoring system to which the present invention is primarily directed.

SUMMARY OF THE INVENTION

It is an object of the present invention to provide a self-contained, reusable wet garment detecting device which may be adapted for use with undergarments of any type, such as disposable paper diaper or cloth diapers.

Another object of the present invention is to provide a device for use with a garment to detect the occurrence of a wet condition within said garment and to produce an electrical output in response to such detection. The detector comprises a housing having front and rear external surfaces for containing electronic components, with the rear of the housing being retainable against the exterior surface of the garment being monitored. A capacitive sensor is located within said housing and is comprised of substantially solid, coplanar first and second conductor plates affixed to a common substrate and which are capacitively coupled to one another. The capacitive sensor is mounted within the housing so that it faces the rear of the housing. The housing also contains electronic circuitry which responds to the electrical capacitance of the capacitive sensor and produces an output signal when the electrical capacitance between the first and second conductors increases to a first pre-determined value resulting from the dielectric effect and the conductivity of the wetness within the garment. The sensor housing is temporarily held in place by a retainer against the outer surface of the garment being monitored. Once a wet garment is detected and changed by an attendant, the sensor is removed and transferred to a dry garment.

A further object of the present invention is to provide a garment wetness detecting device for detecting the presence of a garment wetness condition and transmitting that condition automatically to a remotely located attendant.

A further object of the present invention is to provide a system for remotely monitoring the wetness condition of a plurality of garments such as may be worn by a number of patients in a nursing home. Such a system is comprised of a plurality of garment wetness sensors, each being electronically encoded with a unique address and having an output coupled to a transmitter for transmitting the encoded address of the garment in the presence of a wet garment condition, whereby each of the wetness sensors is affixed to a garment to be monitored. The system further comprises at least one receiver for receiving the transmitted encoded signals, a decoder for determining the address of the source of the transmitted signal, and an annunciator for informing an observer as to the address of the wet garment signal.

A further object of the invention is to provide a wireless paging device in connection with the garment wetness detecting system for transmitting the decoded address of a wet garment to the paging device for directing the attention of an attendant to the address of the wet garment.

Other objects, features and advantages of the present invention will become more apparent upon a reading of the following detailed description of the preferred embodiments of the present invention when read in conjunction with the accompanying drawings.

BRIEF DESCRIPTION OF THE DRAWINGS

FIG. 5 is a perspective representation of the plates of a parallel plate capacitor of the prior art, FIG. 6 is a perspective representation of a coplanar plate capacitor in proximity to a tray providing an experimental source of wetness;

FIG. 7 is a first equivalent circuit diagram of certain capacitive and resistive circuit values;

FIG. 8 is a second equivalent circuit diagram of certain capacitive and resistive circuit values.

FIG. 10 is a depiction of a voltage waveform measured at test point F of the circuit shown in FIG. 9.

FIG. 11 is a depiction of a voltage waveform measured at test point D of the circuit shown in FIG. 9.

FIG. 12 is a depiction of a voltage waveform measured at test point R of the circuit shown in FIG. 9.

FIG. 13 is a depiction of a voltage waveform measured at test point P of the circuit shown in FIG. 9.

FIG. 14 is a depiction of a voltage waveform measured at test point H of the circuit shown in FIG. 9.

FIG. 15 is a depiction of a voltage waveform measured at test point I of the circuit shown in FIG. 9.

DETAILED DESCRIPTION

Figure 1:
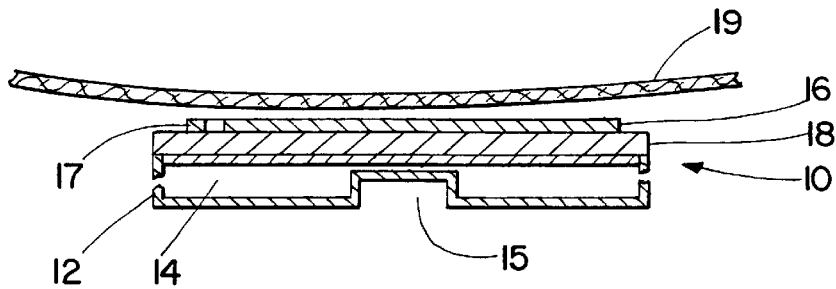
FIG. 1 is a sectional view of a prior art capacitive type wetness detector positioned against the exterior surface of a diaper.
Figure 3:
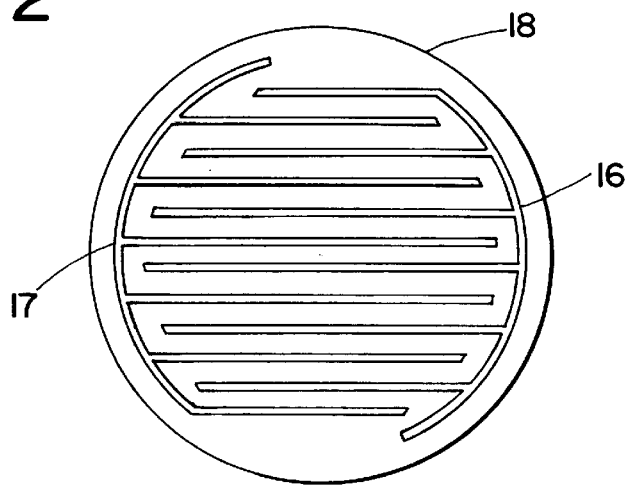
FIG. 3 is a plan view of a prior art capacitive sensor showing the conductive plates as being interleaved.

Referring now in more detail to the drawings, in which like numerals refer to like parts throughout the several views, FIG. 1 and FIG. 3 show a capacitive type sensor 10 according to the prior art as disclosed by Johnson in U.S. Pat. No. 5,469,145. Referring first to FIG. 1, the capacitive sensor 10 is shown in section to be comprised of a housing 12 in which space is provided for circuit components 14, not shown in detail. The housing 12 is generally round and contains a space 15 for an audible alarm, such as a speaker or buzzer, not shown. Affixed to the outside of the housing 12 and positioned in facing contact with garment 20 is a first conductive plate 16 and a second conductive plate 17. Referring additionally to FIG. 3, interleaved plates 16 and 17, separated by a dielectric (air), form a capacitor, which is mounted upon a common, non-conductive substrate 18. The exposed capacitive sensor 10 is held with its conductive fingers 16 and 17 in facing contact with garment 19 by means of an adhesive patch, not shown.

Figure 2:
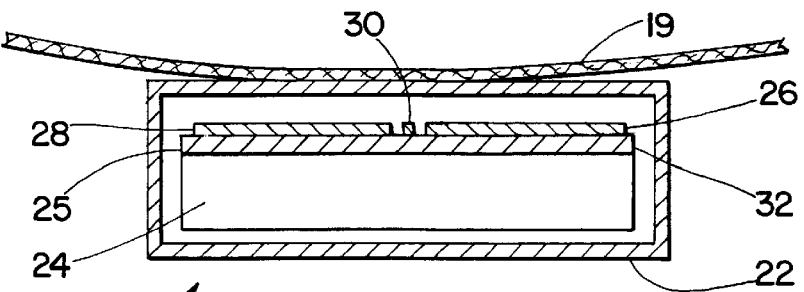
FIG. 2 is a sectional view of the capacitive sensor according to one embodiment of the present invention, mounted within a housing and positioned against the exterior surface of a diaper.
Figure 4:
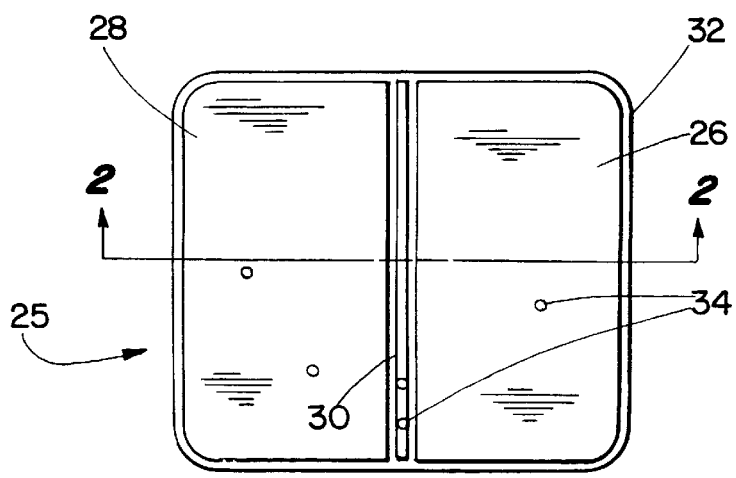
FIG. 4 is a plan view of the capacitive sensor according to one embodiment of the present invention.

In contrast to the prior art capacitive type wetness sensor 10, FIGS. 2 and 4 depict the completely encased, capacitive type sensor 20 of the present invention. Referring first to FIG. 2, capacitive sensor 20 is shown in section to be comprised of a housing 22 in which space is provided for circuit components 24, not shown in detail. The housing 22 is generally rectangular but could be made round or any other shape that would accommodate the necessary internal circuitry 24, as well. The internal circuitry 24, as more specifically detailed in FIG. 9 below, is mounted upon one side of p.c. board 32. On the opposite side and affixed to p.c. board 32 are located a first conductive plate 26 and a second conductive plate 28. Conductive plates 26 and 28 are preferably formed from the conductive foil which comprises one side of p.c. board 32, but could alternately be formed from other conductive plates which may be adhered to or otherwise affixed to one side of the p.c. board. It is also envisioned that the two conductive plates 26 and 28 may ultimately be replaced by a one piece capacitive sensor which may be electrically coupled to the remaining sensor circuitry. As can be seen from FIG. 2, the capacitive sensor 20 is totally contained within housing 22, thus protecting it from becoming soiled and coming into contact with the fingers or skin of the wearer which could cause false triggering.

Figure 9:
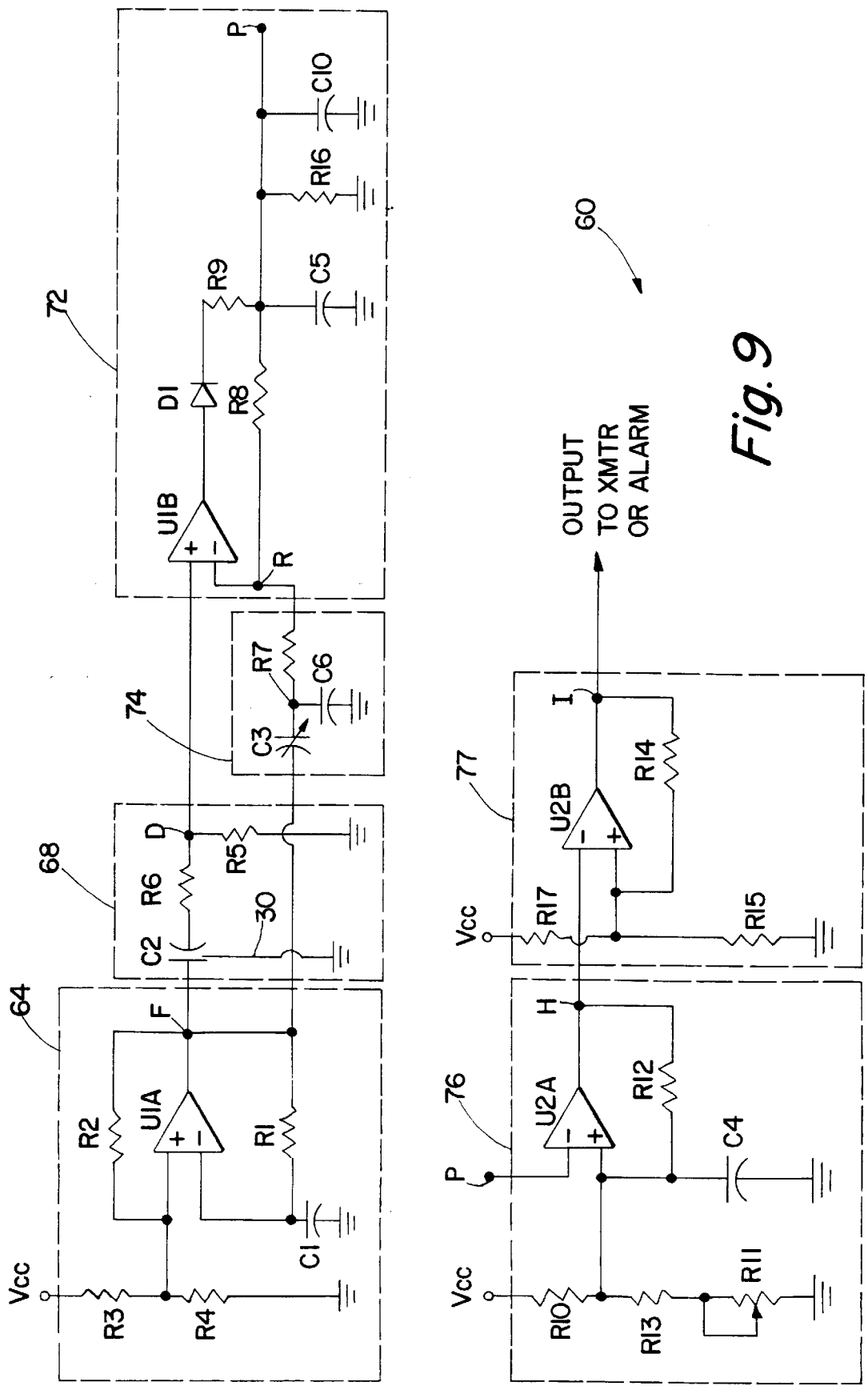
FIG. 9 is an electrical schematic of the capacitive sensor board according to one embodiment of the present invention.

Referring additionally now to FIG. 4, non-interleaved plates 26 and 28, separated by a dielectric (air), form a capacitor C2 for use in the capacitive sensing circuit 68 detailed in FIG. 9, below. The substantially solid plate design of the present invention, as opposed to the interleaved fingers shown in the prior art in FIG. 3, has been shown to provide a much more sensitive capacitive arrangement with a much greater dynamic range and which requires no additional amplification in order to function as a capacitive sensor C2 as depicted in FIG. 9 below. For example, the increase in capacitance is roughly around 50%, e.g., the range for the interleaved sensor the capacitance is around 36 picofarad$_{dry}$(pf) and 53pf$_{wet}$. This represents a dynamic range of about 47%. In contrast, with the capacitive design of the present invention the range of capacitance between dry and wet is typically from around 0.2 pf$_{dry}$ to around 6 pf$_{wet}$, i.e., representing around 2900% dynamic range.

The wetness sensor 20 is secured in facing contact with garment 19 by means of an adhesive pouch, not shown. Alternately, sensor 20 may be attached to garment 19 by using clips, adhesive patches, pre-formed pockets in the garment or other means designed to keep the sensor in close proximity to an area of the garment which is to be monitored for wetness.

Before discussing the specific circuitry employed by the wetness sensor 20 of the present invention, it may be helpful to contrast the operation of the more common parallel plate capacitor with the co-planar capacitor employed in the present invention and how two electrodes, as at 26 and 28 in FIG. 2 may be effective for non-contact detection of wetness.

Referring to FIG. 5, it can be seen that the basic structure of a parallel plate capacitor 40 consists of two plates 41, 43 fixed in parallel to one another separated by a dielectric 42. The value of capacitance depends upon the geometry of the plates 41, 43 of the capacitor as well as the dielectric value of the insulator 42 between them. Assuming that the electrodes are of the same size, the value of capacitance (C) of a parallel plate capacitor, as depicted in FIG. 5, can be generally determined by the formula:

$$C = \epsilon_o \epsilon_r (x^* l)/d + C_f \tag{1}$$

where, $\epsilon_o$=permittivity in vacuo=8.85 pf/m (for air)

$\epsilon_r$=relative permittivity (dielectric constant) with respect to air x=the width of the electrodes l=the length of the electrodes d=the distance between the electrodes $C_f$=capacitance caused by the fringing effect of the electric field between the two electrodes. The value of $C_f$ is usually very small and can be ignored.

In practice, the value of $\epsilon_o$ in free space is essentially the same as that for a gas (e.g., for air, $\epsilon_o$=1.000536). The majority of liquid and solid dielectric materials have dielectric constants ($\epsilon_r$) extending from approximately 2 to 10, e.g. plastic is about $_{2.5}$. However some liquids have much higher values, such as alcohol ($\epsilon_r$=24), distilled water ($\epsilon_r$=80) and salt water ($\epsilon_r$<80).

Referring now to FIG. 6, the general geometry of a capacitor 44 having co-planar electrodes 45, 46 is there depicted. With respect to the present invention, electrodes 45, 46 correspond with electrodes 26, 28 shown in FIG. 2 mounted upon a printed circuit board 25. The electrodes are separated by an insulator (air) 48. The capacitive value of the co-planar capacitor ($C_{total}$), which corresponds to the value of capacitor C2 in FIG. 9, can be determined using the following formula:

$$C_{total} = C_{static} + C_{dynamic} \tag{2}$$

$C_{static}$ depends upon: the distance (d) between the two electrodes 45, 46; the length (l) of the electrodes;, the thickness (h) of the electrodes; the dielectric constant ($\epsilon_r$) of the insulator between the electrodes; the fringing effect ($C_f$); and the stray capacitance ($C_{stray}$). Therefore, $C_{static}$ may be determined by the following formula:

$$C_{static} = \epsilon_o \epsilon_r (x^* h)/d + C_f + C_{stray} \tag{3}$$

where, $\epsilon_o$=permittivity in vacuo=8.85 pf/m (for air)

$\epsilon_r$=relative permittivity (dielectric constant) with respect to air x=the width of the electrodes l=the length of the electrodes d=the distance between the electrodes h=the thickness of the electrodes $C_f$=capacitance caused by the fringing effect of the electric field between the two electrodes. The value of $C_f$ is usually very small and can be ignored.

The capacitive value for $C_{dynamic}$ is the actual sensing component of formula (2) which depends upon the following variables: the dielectric of the sensed media in proximity to the electrodes ($\epsilon_{rm}$); the distance of the sensed media to the electrodes (y); the area of the electrode adjacent to the sensed media (l*x); and the dielectric constant value of the insulator between the electrodes and the sensed media ($\epsilon_{rp}$).

Referring additionally to FIG. 7, the $C_{dynamic}$ has two components $C_r$ and $C_d$, and may be determined by the following formula:

$$C_{dynamic} = C_r + C_d \qquad (4)$$

where $C_d$=the capacitance caused by the dielectric constant of the media ($\epsilon_{rm}$) and $C_r$ is the capacitance caused by the conductivity of the media. The value of $C_r$ may be determined by the following formula:

$$C_r = \epsilon_o \epsilon_{rp} (x*l)/2y \qquad (5)$$

Ignoring the small fringing effect capacitance ($C_f$), equation (2) may be rewritten as follows:

$$C_{total} = \epsilon_o \epsilon_r (x*h)/d + C_{stray} + C_d + \epsilon_o \epsilon_{rp}(x*l)/2y \qquad (6)$$

By design, the effect of the first two terms of equation (6), ($\epsilon_o \epsilon_r (x*h)/d + C_{stray}$) can be reduced, thus increasing the effect of the last two terms, ($C_d + \epsilon_o \epsilon_{rp}(x*l)/2y$).

An experiment was conducted to confirm the validity of equation (6). Two coplanar electrodes were etched on a printed circuit board in much the same fashion as depicted in FIG. 4, each of the electrodes having the following characteristics:

l=1.5 inches
h=0.0007 inch
d=0.075 inch
x=0.5 inch

The etched, co-planar capacitive sensor 25 was then connected to an oscillating voltage of 3Vdc at 12 kHz in a circuit such that the output voltage could be monitored. A plastic container, similar to that depicted at 50 in FIG. 6, having a wall thickness of 0.015 in, was placed in proximity to the etched sensor 25 and alternately filled with various liquid materials. The circuit output voltage was recorded for each of the various liquids which were placed in proximity to the sensor. These values are shown in Table 1.

TABLE 1

| Media | $V_{out}$ (mv) | Change with respect to air (mv) |
|---|---|---|
| Air (empty) | 320 | 0 |
| Alcohol | 540 | 220 |
| Water (H₂O) | 836 | 516 |
| Salt Water | 1230 | 910 |
| Mercury (Hg) | 1320 | 1000 |

The measured values for $V_{out}$ as recorded in Table 1 may be explained by referring back to FIG. 7. Mercury (Hg) is a very good conductor, so essentially resistance R=0, and capacitance $C_d$=0 and would thus drop out of the equivalent circuit shown, leaving only $C_{R1}$ and capacitances $C_{R2}$ and $C_{static}$. Therefore the mercury set as the third plate to make the two capacitors in series with the dielectric of the container 50. The measured output of the sensor 25 with mercury in the container 50 was approximately 1320 mVdc.

With respect to water (H₂O)), while initially it is pure, it contaminates quickly. Under ideal conditions, the equivalent circuit for water would be that capacitances $C_{R1}$ and $C_{R2}$ and resistance R would drop out of the circuit shown in FIG. 7, thus leaving $C_d$ in parallel with $C_{static}$. The measured output of the sensor 25 with water in the container 50 was approximately 836 mVdc.

Next, salt (NaCl) was added to the water. With the salt added, the voltage output raised from 836 to 1230 mVdc. While the dielectric of the salt water decreased the output voltage of the circuit increased. This is due to a corresponding decrease in the resistivity of the water. FIG. 7 shows the equivalent circuit. The percentage increase can be shown by the following formula:

$$\% = (Vdc_{salty} - Vdc_{water})/Vdc_{water} *100 = (1230-836)/836*100 = 47\%$$

Alcohol was also tested because it has a lower dielectric constant than water and because it is not conductive. Referring to FIG. 7, the equivalent circuit for alcohol would be the capacitances $C_{R1}$ and $C_{R2}$ with resistance R dropping out of the circuit, thus leaving capacitance $C_d$ in parallel with $C_{static}$. Pure water produced an output voltage of 836 mVdc. Alcohol produced a voltage of 540 mVdc. Subtracting the $Vout_{empty}$ from each of these results yields the following outputs attributable to the liquids alone: $Vout_{alcohol}$=220 mVdc and $Vout_{water}$=516 mVdc. The ratio of outputs of water to alcohol is 516/220=2.4. The corresponding relationship between their respective dielectric constants is 80/24 =3.33.

These two ratios approximate one another. Analysis of Table 1 is shown to be attributable to the conductivity of the materials and not just their respective dielectric constants.

In the application of the co-planar sensor 25 in the detection of wetness within a garment 19, the following tests were conducted. Referring to FIG. 2, copper electrodes 26, 28 were etched onto a printed circuit (p.c.) board 32 of a composite, fiber-reinforced type. A ground line 30 is also etched onto the p.c. board 32 to minimize the capacitance of $C_{static}$. The p.c. board was 0.062 in thick and had a dielectric constant of 3.4.

The p.c. board 32 was fitted with electronic components generally at 24. The populated circuit board 32 and sensor 25 were then mounted within a housing 22. The housing 22 was made of plastic having a thickness of 0.020" and had a dielectric constant ($\epsilon_{rp}$) of 2.5. The housing 22 was then placed against a plastic, disposable diaper, shown generally at 19. The Plastic diaper cover was measured to be 0.003 in and had a dielectric constant ($\epsilon_{rd}$) of 1.5. All dielectric constants were determined experimentally.

The electrical model for the above wetness detector 20 being placed in contact with a disposable diaper 19 is depicted in FIG. 8. Capacitance $C_d$ is the capacitance caused by the dielectric constant of urine ($\epsilon_r$<80). $C_{P1}$ and $C_{P2}$ are the capacitances created by the housing 22 in the presence of urine in the garment 19 according to the following formula:

$$C_P = \epsilon_o \epsilon_{rp}(x*l)/y = 0.225*2.5(1.5*0.5)/0.02 = 21.1 pf \qquad (8)$$

where $\epsilon_{rp}$=2.5 and the thickness of the housing is 0.020 in. Capacitance $C_{D1}$ and $C_{D2}$ are the capacitances caused by the garment 19 in the presence of urine according to the formula:

$$C_D = \epsilon_o \epsilon_{rd}(x*l)/1y = 0.225*1.5(1.5*0.5)/0.003 = 84.3 pf, \qquad (9)$$

where $\epsilon_{rd}$=1.5 and the thickness of the plastic cover of the diaper is 0.003 in.

For urine, the value of resistance R is assumed to be 0 since urine is a very good conductor The capacitance $C_R$ is the value of $C_P$ in series with $C_D$ for each of the two electrodes. In the above described test the value of capacitance $C_R$ can be computed as follows:

$$C_{R1 \text{ or } 2} = (C_P * C_D)/(C_P + C_D) = (21.1*84.3)/(21.1+84.3) = 16.8 pf \quad (10)$$

$$C_{R \text{ total}} = 16.8/2 = 8.4 pf \quad (11)$$

Therefore, $C_{dynamic} = 8.4 pf + C_d$.

From the test using pure water and salt water, it was shown that there was a 47% increase in the voltage output. Therefore, capacitance $C_d$ is equal to approximately 17.9 pf.

The value of capacitance $C_{static}$ is the inherent capacitance of the circuitry, which can be nullified by zeroing circuitry, discussed below. From these calculations, it can be seen that the dynamic range of the sensor can be increased by increasing the value of $\epsilon_{rp}$.

Referring now to FIG. 9, the electronic circuit for the capacitive wetness sensor 20 is shown generally at 60. Functionally identifiable circuit components are shown there using dashed lines. The first circuit component is oscillator 64 which, in the preferred embodiment, has been designed for a frequency output of around 12 khz. There it can be seen that the circuit is powered by Vcc, which in the preferred embodiment is an on-board 3 volt battery. The circuit has also been designed for very low power consumption because it is desirable that the battery operated capacitive sensor 60 function a long time between battery changes. Comparator U1A, available commercially as part number LMC6762, is a CMOS comparator which consumes about 10 $\mu$a per op amp. The oscillator basically oscillates at a frequency determined by the values of resistor R1 and capacitor C1 connected between the output pin and the "−" pin of U1A according to the formula $\frac{1}{1.4}(R1)(C1)$. Resistors R2, R3 and R4 connected to the "+" pin of U1A, are provided to set a bias for op amp U1A. The connection of R2 between the "+" input and the output pin of U1A, test point F, provides the feedback loop which causes U1A to oscillate, providing a pulsed, 3Vdc output. The circuit design takes into account the slew rate, or rise time, of pulsed output from U1A, which is rated at a nominal 300 ns. The values for R2, R3 and R4 are chosen to be high in order to keep the current consumption low, thereby conserving power.

Referring additionally to FIG. 10, the pulsed output waveform from oscillator circuit 64 at test point F is shown. Looking once again to FIG. 9, the output of oscillator circuit 64 is shown to be connected to capacitive sensor circuit 68. The sensor circuit 68 is comprised of capacitor C2, (shown at 25 in FIG. 4), coupled to resistor R6 and R5.

This combination of components forms a differentiator, the wave form of which is shown graphically as FIG. 11. Resistor R5 determines the time constant because resistor R6 is very small compared to resistor R5. Resistor R6 is provided to protect the "+" input of op amp U1B.

Referring additionally to FIG. 4, the capacitive sensor 25 is basically comprised of two electrodes, nominally 0.5 in×1.5 in, set together in the same plane separated by a space, nominally 0.075 in. The sensitivity of the capacitive sensor 25 is not a function of the distance between electrodes 26, 28, however the gap between electrodes is kept small to conserve on space. The electrodes 26, 28 of the capacitor may be comprised of copper foil on one side of a printed circuit board 32 upon which the sensor circuit 60 components are mounted. Alternately, the electrodes could be fabricated from other conductive materials and mounted to a common substrate, such as at 32.

As shown in FIG. 4, a ground line 30 is provided between the two electrodes 26, 28 of capacitor C2 which provides a common circuit ground without encroaching upon the surface area of the electrodes. To conserve on space, sensor circuit 60 utilizes mostly surface-mount components. Alternately, a custom made integrated circuit could be fabricated to replace the sensor circuit 60 components. The central ground line 30 also eliminates some effect of the initial value of the capacitance affects associated with the edges of the two electrodes 26, 28.

The input to capacitor C2 is a 3.0V peak square wave pulses at 12 khz. Referring to FIG. 11, the output waveforms of the sensor circuit 68, at test point D, when dry, such as at time $T_0$ through $T_1$, are both positive and negative going voltage spikes of around 100 mv. When wet, such as at time $T_1$ through $T_3$, the peak amplitude of the signal will increase to around 3-4 times greater than as when dry, to around 400 mv, depending upon the value of resistor R5. R5 is of critical value since it cannot be made too high a value because of noise. On the other hand, it needs to be a value which will produce a voltage of sufficient amplitude to trigger the next section of sensor circuit 60, the peak detector circuit 72.

The output of sensor circuit 60 is provided to the input of peak detector/bridge circuit 72 at the "+" pin of op amp U1B. Related to peak detector circuit 72 is zeroing circuit 74 which is comprised of capacitor C3 and C6. This circuit is connected to the negative input of U1B for zeroing the initial value of the voltage at test point P. The voltage value at test point P is a Vdc value which corresponds to reference voltage values of representing a "dry" condition and a "wet" condition. For a corresponding waveform of the voltages at test point P, reference may be had to FIG. 13.

Initially, the d.c. voltage level at test point P is ideally close to 0Vdc. This voltage level is somewhat variable by adjustment of capacitor C3. The effect of adjusting C3 in combination with fixed capacitor C6 is to eliminate much of the stray circuit capacitance caused by the presence of components on the opposite side of p.c. board 32 from the foil electrodes 26, 28 of the sensor capacitor C2 25. The combined capacitance of capacitors C3 and C6 is the zeroing capacitance provided to resistors R7 and R8. Resistors R8 and R5 are of the same value and resistors R6 and R7 are provided as equal values in order to balance the peak detector/bridge of op amp U1B in such a way as it is always constant. The only change in the balance of the bridge is between the wetness and dryness states. The voltage waveform of the circuit at test point R is shown in FIG. 12.

The peak d.c. voltage out of the peak circuitry 72, at test point P, is basically the d.c. voltage corresponding to an initial value of about 25 mv by finely adjusting capacitor C3. When the circuit has been adjusted to produce a 25 mv initial output to represent a "dry" condition, the peak value output of the original 400 mVdc pulses is affected to be 200 mVdc in the presence of a "wet" condition. This represents an eight-fold (0.025:0.200) voltage shift between a dry and wet states. While this peak detection and zeroing is the expense of cutting down the peak voltage level from 400 mVdc to 200 mVdc, there is a significant increase in the dynamic range between wet and dry conditions—from 4:1 to 8:1.

Still referring to FIG. 9, diode D1 is a forward biased standard peak detection diode which operates only when the output from U1B is positive. Resistor R9 is provided to prevent the overshoot of the peak detector circuit 72. An important aspect of the peak detector circuit 72 is capacitor network formed by parallel capacitors C5 and C10. The network formed by capacitor C5 and resistor R16 is provided to perform peak detection. Capacitor C5 stores the peak voltage value that was detected and is large enough to provide a large enough time constant, in combination with resistor R16, to prevent false triggering of the circuit should wetness sensor 20 loose contact with the surface of the garment 19 to which it is attached. In one embodiment of the invention the RC time constant is nominally set to around 44 seconds ((C5+C10)×R16=20 μf×2.2 MΩ=44 secs.).

The amount of time that the voltage is stored is an important factor in the present invention in order to minimize the number of false dryness indications that might occur during temporary shifts of the wearer of a wet garment 19 with respect to wetness sensor 20. In contrast, if the RC time constant were designed to be short and the wearer of the garment 19 were to play with wetness sensor 20, i.e., move it up and down, this could result in a multi-triggering of the transmitter circuit 78, discussed infra. For example, referring to FIG. 13, time $T_3$ represents the moment at which wetness sensor 25 is temporarily removed from the surface of garment 19. The dashed line beginning at time $T_3$ represents the discharge of an RC network having a short delay. In this respect the faster discharging circuit will arrive at $V_{low}$ sooner than a slower discharging RC network, as incorporated into the preferred embodiment by resistor R16 and capacitor C5. As can be seen from FIG. 13, the output of the peak detector, at test point P, is a solid d.c. voltage.

The zeroed and peak detected voltage at test point P is, in turn, provided to comparator/hysteresis circuit 76. The comparator/hysteresis circuit 76 is centered around comparator U2A, such as may be provided commercially as a model LMC6762. Resistor R12 is connected between the output of the comparator U2A and the positive input to provide positive feedback to U2A. The $V_{ref}$ is a dynamic voltage value corresponding to $V_{low}$ or $V_{high}$ which is dependent upon the output of comparator U2A. Capacitor C4 is provided between the positive input to U2A and ground in order to filter out some of the a.c. noise in the circuit.

The peak voltage value, from test point P, derived from the previous circuit section is fed into the negative input of comparator U2A. The value of the peak voltage is compared to the value of the $V_{ref}$ d.c. voltage provided by network of resistors R10, R11, R12 and R13. In a dry, steady state condition the output of op amp U2A, at test point H, is high. The waveform for test point H is depicted in FIG. 14. The voltage values of the "wet" and "dry" triggering points in the circuit are designated $V_{high}$ and $V_{low}$. $V_{high}$ may be computed as follows:

$V_{high}=R_s/(R_s+R_p) \times V_{cc}$, where $R_s$=the series resistance of resistors R11 and R13, and $R_p$=the parallel resistance of resistors R10 and R12.

$V_{low}$ may be computed as follows:

$V_{low}=R_p(R_p+R10) \times V_{cc}$, where Rp=the parallel resistance of $R_s$ and R12.

The value of R13 is about $_3$ kΩ and resistor RI I in one embodiment of the invention is set to around 16 kΩ. Therefore, when the output of comparator U2A is high, the triggering point for the circuit is accordingly, $V_{ref}=V_{high}=$ 104 mVdc.

In operation, when the capacitive sensor 25 senses wetness, the comparator/hysteresis circuit 76 will respond in the following fashion. Resistors R10 and R13 and R11 are fixed at their respective values. However, resistor R12, normally at 3 Vdc and in parallel with resistor R10 during the "dry" state, will go to ground. When resistor R12 runs to ground, it becomes in parallel with resistors R11 and R13, and $V_{ref}$ now becomes $V_{low}$=52 mVdc. Referring to FIG. 14, the comparator/hysteresis circuit 76 performs in the following fashion: the voltage output of comparator U2A is high (from times $T_0$ through $T_2$) until voltage at test point P, i.e., the output of the peak detector 72 reaches 104 mVdc (at $T_2$), at which time the voltage out of comparator U2A goes to 0Vdc (when resistor R12 goes to ground). Once triggered, the output of U2A will continue to be 0Vdc regardless of how much more wetness the detector senses, as shown in the FIG. 14 from times $T_2$ through $T_4$. Once the wetness condition is removed, as at time T4, the output of the comparator/hysteresis circuit 76 returns to its high state.

The voltage zone between $V_{high}$ (104 mVdc) and $V_{low}$ (52 mVdc) is referred to as the hysteresis zone, wherein the state of the output of comparator U2A will not change from one to the other. When the wetness decreases, due to the source of the wetness being removed from the area of the sensor, such as at time $T_3$, then the output of the peak detector will decrease. Causes of decreased wetness sensing can include the removal of the wet garment 19, diffusion of the liquid in the garment by absorption, evaporation, etc. or removal of the wetness sensor 25 from the surface of the garment. It is undesirable that small fluctuations in wetness would change the "wetness" state output from the U2A. Otherwise, a wet garment 19 could go unattended or a monitoring receiver, as at 62 in FIG. 16, could see multiple triggers for a single incident. It is for this reason that the hysteresis designed into the comparator/hysteresis circuit 76 is important.

The output of the comparator/hysteresis circuit 76 may be provided to inverter circuit 77. In one embodiment of the invention this is desirable since the transmitter 78 used in the circuit used to notify a receiver 80 of a wetness condition in the presence of a "high" signal, while the output of comparator/hysteresis circuit 76 is "low" in the presence of a wetness condition. Referring to FIGS. 10 and 11, is can be seen that the voltage at test point I, that is the output of the inverter circuit 77, is "low" when its input, at test point H, is "high" and vice versa. This circuit would not be necessary if a transmitter 78 was chosen which was active in the presence of a "low" output.

In inverter circuit 77, resistor R14, connected between the output and positive input of U2B, provides positive feedback to the comparator. Resistors R15 and R17 form a voltage divider network and are provided to supply the reference voltage to U2B. The circuit behavior is much the same as comparator/hysteresis circuit 76 except the negative input voltage value at comparator U2B is supplied as a digital value of either 0Vdc or 3Vdc.

Figure 16:
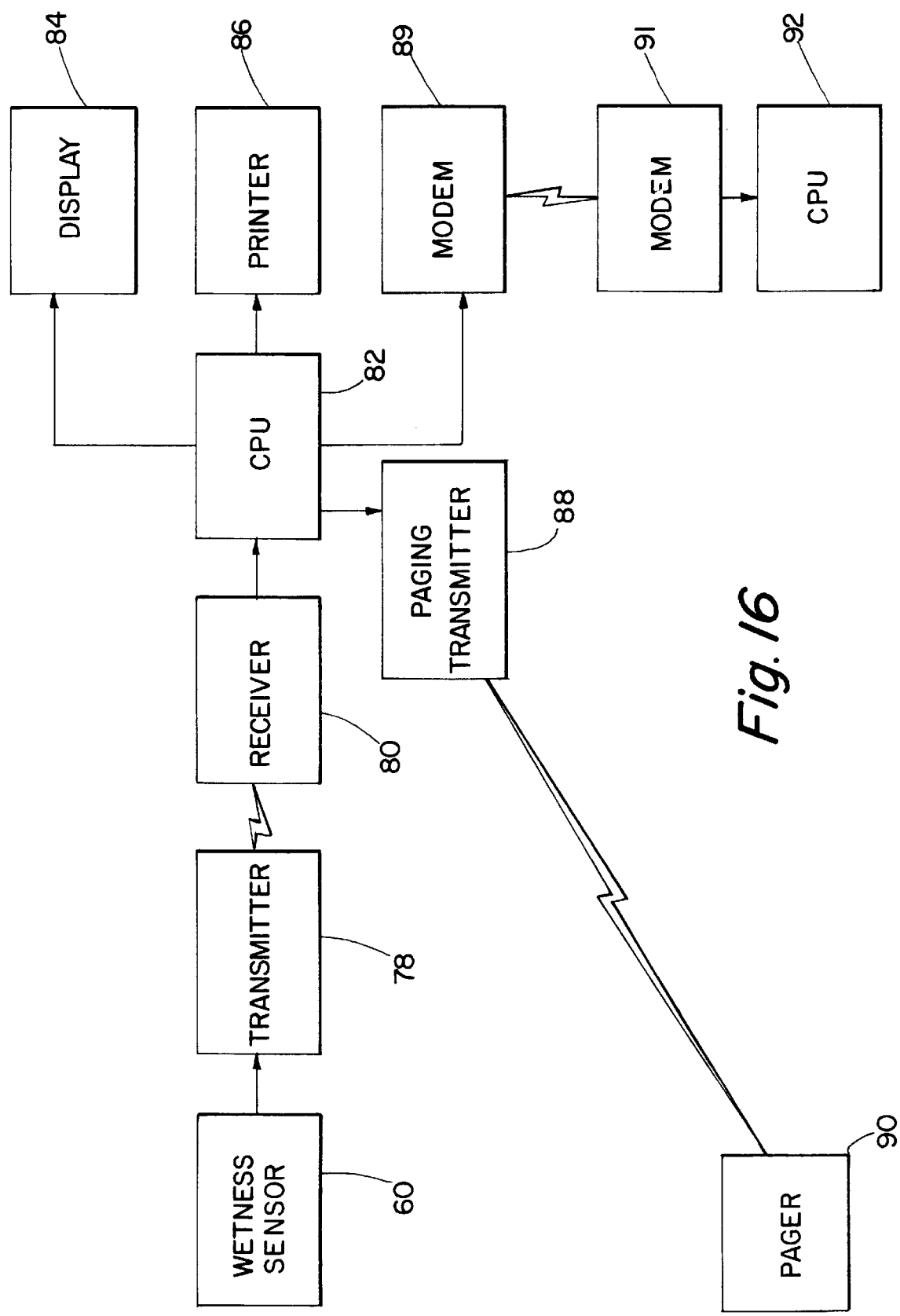
FIG. 16 is a system block diagram of one embodiment of the present invention.

Referring next to FIG. 16, the output of wetness sensor circuit 60 is provided to a battery operated transmitter 78 for signaling a remote receiver 80 of a wetness condition. The transmitter 78 is preferably of the 900 Mhz type as is commercially available from Inovanics Corporation, as a model FA203S although other frequencies could be employed, as well. The transmitter 78 in one embodiment of the invention is addressable through the selection of dip switches or the like, such that the source of a transmitted signal may be identified. This is highly desirable in an application wherein a number of wetness sensors 20 may be employed, such as a nursing home, and it is important that each transmitted signal be easily identifiable. In this regard, monitoring personnel located at a receiver 80 can identify the source of the wetness signal and timely dispatch the appropriate care giver to attend to the removal of the wet garment 19.

In the preferred embodiment of the invention, the "wetness" signals arriving at receiver 80 are monitored by a computer (CPU) 82 and logged into a database using software, such as commercially available from Zaggie, Inc. as Caretrac™ software. In this regard a complete, time-stamped history of the patient in a nursing home, for example, may be kept automatically. This can help ensure that they are receiving proper care while also assisting the nursing staff by providing vital information regarding a patient's bodily functions. In addition to maintaining a database of patient information, CPU 82 can also function to periodically remind care givers that a wet garment 19 still needs attention or that a given patient is not urinating regularly.

The CPU 82 is preferably connected to a display 84 enabling the monitoring personnel to visually identify the source of the transmitted wetness signals, patient information database and the like. A printer 86 may be provided to create a hard copy of information displayed on the display 84 or to print reports from data contained in the CPU 82 database. Additionally, a paging transmitter 88 may be in communication with CPU 82 such that pagers 90, being worn by the care givers in a facility, may be automatically dialed by the CPU in the presence of a wetness condition and provided with the "address" of the source. In this fashion, the care givers may attend to the changing of wet garments 19 in a timely fashion without the requirement of interacting with the monitoring personnel. In the preferred embodiment of the invention, once the care giver has corrected the wetness condition at a particular patient "address", that fact is sent to the receiver 80, reflected upon display 84 and stored in the patient's history by CPU 82. Additionally, the address of a wetness condition may be supplied by CPU 82 to first modem 89 which, in turn, is directed to communicate with a second CPU 92 via a second modem 91. In this manner, a support and administration station may be kept informed as to the attention being provided to patients under the care of the facility.

The invention has been disclosed and described herein in terms of preferred configurations and methodologies. However, it will be obvious to those of skill in the art that numerous variations of the illustrated embodiments could be implemented within the scope of the invention. For example, the transmitter 78 included in the preferred embodiment might easily be replaced with a visual indicator, such as a flashing LED, or a small speaker device for audibly notifying an attendant when the garment becomes wet. Further, in addition to the capacitive type sensor illustrated it is also envisioned that other types of sensors, such as resistive, inductive, thermal and photoelectric could be effectively implemented to perform the same functions in an acceptable way. These and other additions, deletions, and modifications might well be made to the exemplary embodiments illustrated herein without departing from the spirit and scope of the invention as set forth in the following claims.

We claim:

1. An apparatus for use with a garment to detect the occurrence of a wet condition within said garment and to produce an electrical output in response to such detection, said apparatus comprising:

a housing having front and rear external surfaces for containing electronic components, the rear of said housing being retainable against the exterior surface of said garment;

a capacitive sensor located within said housing, said sensor being comprised of substantially solid, coplanar first and second conductor plates affixed to a common substrate, being capacitively coupled to one another and having a coplanar grounding strip located intermediate them, said capacitive sensor being positioned facing the rear of said housing;

electronic circuitry within said housing responsive to the electrical capacitance of said capacitive sensor for producing an output signal when said electrical capacitance between said first conductor and said second conductors increases to a first predetermined value as a result of the dielectric effect and conductivity of wetness within said garment; and a retainer for removably affixing said housing to the exterior surface of said garment.

2. The apparatus of claim 1 wherein said retainer for removably affixing said housing to the surface of the garment comprises an adhesive flap sized to be adhered to the exterior surface of said garment with said housing interposed between said flap and said garment surface.

3. The apparatus of claim 1 wherein said output is provided to a transmitter for transmitting a signal in the presence of a wet garment condition.

4. The apparatus of claim 1 wherein said circuitry further comprises an alarm component coupled to said output signal for actuation of an alarm in the presence of a wet garment condition.

5. A system for remotely monitoring the wetness condition of a plurality of garments, said system comprising:

a plurality of garment wetness sensors, each sensor being located within a housing and being comprised of substantially solid, coplanar first and second conductor plates affixed to a common substrate, said plates being capacitively coupled to one another and having a coplanar grounding strip located intermediate them, said capacitive sensors each being positioned facing the rears of their respective said housings and each being electronically encoded with a identifying address and having transmitter for transmitting said encoded address in the presence of a wet garment condition, whereby each of said wetness sensors is affixed to a garment to be monitored;

at least one receiver for receiving said encoded signals and having a decoder for determining the address of the source of said signal; and an annunciator for informing an observer as to the address of the wet garment signal.

6. The system of claim 5 further comprising a modem in communication with at least one pager whereby the source of a wet garment signal is transmitted to and displayed upon said pager.

* * * * *